United States Patent
Webster et al.

(10) Patent No.: US 7,013,713 B2
(45) Date of Patent: Mar. 21, 2006

(54) LUBRICITY TESTER FOR DIESEL FUELS

(75) Inventors: Gary Webster, Ottawa (CA); Clint Gray, Nepean (CA); Dennis Raymond, Gatineau (CA)

(73) Assignee: Advanced Engine Technology Ltd., Nepean (CA)

( * ) Notice: Subject to any disclaimer, the term of this patent is extended or adjusted under 35 U.S.C. 154(b) by 0 days.

(21) Appl. No.: 10/865,756

(22) Filed: Jun. 14, 2004

(65) Prior Publication Data

US 2005/0016262 A1  Jan. 27, 2005

Related U.S. Application Data

(60) Provisional application No. 60/320,271, filed on Jun. 13, 2003.

(51) Int. Cl.
*G01N 19/08*  (2006.01)

(52) U.S. Cl. .................................... 73/53.06
(58) Field of Classification Search .................. 73/10, 73/53.05, 53.06
See application file for complete search history.

(56) References Cited

U.S. PATENT DOCUMENTS

| | | | | |
|---|---|---|---|---|
| 2,019,948 A | * | 11/1935 | Boerlage | 73/10 |
| 3,045,471 A | * | 7/1962 | Chapman et al. | 73/10 |
| 3,113,449 A | * | 12/1963 | Morgan | 73/10 |
| 3,143,877 A | * | 8/1964 | Moyer | 73/53.05 |
| 3,302,447 A | * | 2/1967 | Mertwoy et al. | 73/10 |
| 3,939,690 A | * | 2/1976 | Kuss et al. | 73/9 |
| 4,228,674 A | * | 10/1980 | Mertwoy | 73/10 |
| 5,184,505 A | * | 2/1993 | van den Berg | 73/53.05 |
| 6,070,456 A | | 6/2000 | Cameron et al. | |
| 6,129,772 A | * | 10/2000 | Weers et al. | 44/385 |
| 6,546,782 B1 | * | 4/2003 | De La Cruz et al. | 73/7 |
| 6,783,561 B1 | * | 8/2004 | Erdemir | 44/314 |
| 6,840,082 B1 | * | 1/2005 | Evans | 73/9 |
| 2003/0045435 A1 | * | 3/2003 | Erdemir | 508/156 |

FOREIGN PATENT DOCUMENTS

| | | | | |
|---|---|---|---|---|
| GB | 2183347 A | * | 6/1987 | |
| GB | 2194060 A | * | 2/1988 | |
| JP | 09236536 A | | 9/1997 | |
| JP | 2004061341 | | 2/2004 | |
| WO | WO 9115763 A1 | * | 10/1991 | |

OTHER PUBLICATIONS

Falex Tribology "Ball on Three Disk Tests for Evaluation of Rolling Emulsions" Sep. 2001, two pages.*

* cited by examiner

*Primary Examiner*—Hezron Williams
*Assistant Examiner*—John Fitzgerald
(74) *Attorney, Agent, or Firm*—Marks & Clerk; Richard J. Mitchell

(57) ABSTRACT

An apparatus for testing lubricity of a fuel includes a testing chamber for holding a sample of the fuel to be tested; an inlet for admitting the sample to the testing chamber; and an assembly for sealing the testing chamber to prevent moisture transfer during admission and testing of the fuel. In this way, more consistent results are obtained.

13 Claims, 4 Drawing Sheets

| Fuel Designation and Test Condition | WSD at 45% R.H. Ambient Conditions (Old BOTD Test) | WSD at 45% R.H. Ambient Conditions (New BOTD Test) |
|---|---|---|
| Ref. Fuel (exposed to 45% R.H.) | 655 | 656 |
| Ref. Fue (18% R.H. in drum) | 626 | 558 |
| Ref. Fuel (18% R.H. in drum) + Additive A1-02 (50 ppm) | 598 | 485 |
| Ref. Fuel (18% R.H. in drum) + Additive A3-02 (50 ppm) | 648 | 460 |
| Ref. Fuel (exposed at 0% R.H.) | NA | 372 (23% Ambient R.H.)* |

FIG. 7

LUBRICITY TESTER FOR DIESEL FUELS

CROSS REFERENCE TO RELATED APPLICATION

This application claims the benefit under 35 USC 119(e) of prior U.S. provisional application No. 60/320,271 filed on Jun. 13, 2003.

FIELD OF THE INVENTION

The present invention relates to lubricant testing. Mores specifically, the present invention relates to a lubricity tester for diesel fuels.

BACKGROUND OF THE INVENTION

Diesel engines rely on fuel as a lubricant for their internal moving components. The lubricity of the fuel affects the wear between two metal parts that are in contact. Wear due to the friction between these parts will cause failure of the components if there is insufficient lubricity. The use of a high lubricity fuel may reduce the wear and increase component life.

Lubricity is defined as the property of a lubricant that causes a difference in friction under conditions of boundary lubrication when all the known factors except the lubricant itself are the same. The lower the friction the higher the lubricity. [Kajdas, C., S. S. K. Harvey, and E. Wilusz, Encyclopedia of Tribology, Elsevier, N.Y., 1990.]. One method of testing lubricity is referred to as the Ball on Three Disks method (BOTD). The BOTD system is used to evaluate the lubricity of fuel used in diesel engines.

The main components of a typical BOTD system are:

1) a lubricity test machine (for example, Falex) with timer and hollow (internal taper) rotating shaft which houses the ceramic test ball 2) A two-piece fuel reservoir (upper and lower halves) which when assembled houses a teflon anti-vibration pad, metal disk holder, three steel test disks and the test fuel 3) a lever arm with fulcrum, weight and small metal ball at one end which is used to apply a force to the bottom of the 2 piece fuel reservoir.

Upon completing an intensive cleaning procedure the BOTD components are assembled for testing The anti-vibration pad is inserted into the inside bottom of the lower portion of the fuel reservoir. The disk holder is then placed on the anti-vibration pad and the 3 test disks are place in the disk holder. The ceramic test ball is placed in the lower end of the hollow (internal taper) shaft of the test machine.

The upper portion of the fuel reservoir is then threaded into the lower portion of the fuel reservoir. The upper portion of the fuel reservoir contacts the disk holder centering it and preventing it from rotating during the test. The test fuel is then added through a large opening in the center of the top of the upper portion of the fuel reservoir using the glass syringe and 5 micron Teflon™ filter.

the base of the fuel reservoir, which has a small depression or socket in the center, is then placed on top of the small metal ball on one end of the lever arm. The lever arm is then placed in the fulcrum with the weight nearest the fulcrum. The lever arm and fuel reservoir assembly is then rotated such that the test machine shaft and test ball assembly passes through the large opening in the top of the fuel reservoir until the test ball contacts the test disks.

Once the assemblies are in place as described above, the timer on the test machine is set for 45 minutes, and the start button is pressed causing the test machine ball and shaft to rotate with the ball contacting the disks during rotation. The weight on the lever arm is then gradually pulled towards the outer end of the lever arm, thereby increasing the force applied to the fuel reservoir at the opposite end of the lever arm and correspondingly the contact force between the disks and ball.

Upon completion of the test the assemblies are disassembled and the disks removed for evaluation. Due to the relative motion and contact force between the ball and disks during the test a wear scar is generated on the metal disks. The fuel in the fuel reservoir provides some measure of lubrication between the ball and disks. As such the size of the wear scar on the disks is related to the lubricity characteristics of the fuel. The disks are placed in a holder, and a traveling microscope with dial indicator is used to determine the diameter of the wear scar on the disks. A large wear scar indicates a fuel with poor lubricity and a small wear scar indicates a fuel with good lubricity.

It has been found that this method has the tendency to produce inconsistent results. The reason why has not been apparent.

SUMMARY OF THE INVENTION

A lubricity tester for diesel fuels is disclosed. The inventors have found surprisingly that the ambient air humidity has a pronounced effect on the lubricity of test fuels as determined by the BOTD test rig. They have found that the prior art BOTD system allows direct contact between the fuel and ambient air, thereby skewing the true lubricity characteristics of the test fuel sample. The embodiments of the BOTD system according to principles of the invention is to essentially eliminate contact between a test fuel and the ambient air around the BOTD test machine so as to ensure that the moisture content of the fuel does not change during testing.

Thus, according to one aspect, the invention provides an apparatus for testing lubricity of a fuel, comprising a testing chamber for holding a sample of the fuel to be tested; an inlet for admitting said sample to the testing chamber; and an assembly for sealing the testing chamber to prevent moisture transfer during admission and testing of the fuel.

The novel apparatus in accordance with the invention has been demonstrated to produce significantly more consistent results over multiple samples than was found possible with the prior art.

A further aspect of the invention provides a method of testing the testing lubricity of a fuel, comprising the steps of extracting a fuel sample from a source of fuel to be tested; transferring said fuel sample to a testing chamber without exposing said fuel sample to ambient air; and performing a lubricity test on said sample in said testing chamber without exposing said fuel sample to ambient air so that the moisture content of the fuel in said sample is substantially the same as the moisture content of the fuel in said source.

Other aspects and advantages of embodiments of the invention will be readily apparent to those ordinarily skilled in the art upon a review of the following description.

BRIEF DESCRIPTION OF DRAWINGS

Embodiments of the invention will now be described in conjunction with the accompanying drawings, wherein:

FIG. 7 is a comparative table comparing the old and novel BOTD system;

DETAILED DESCRIPTION

This invention will now be described in detail with respect to certain specific representative embodiments thereof, the materials, apparatus and process steps being understood as examples that are intended to be illustrative only. In particular, the invention is not intended to be limited to the methods, materials, conditions, process parameters, apparatus and the like specifically recited herein.

Figure 1:
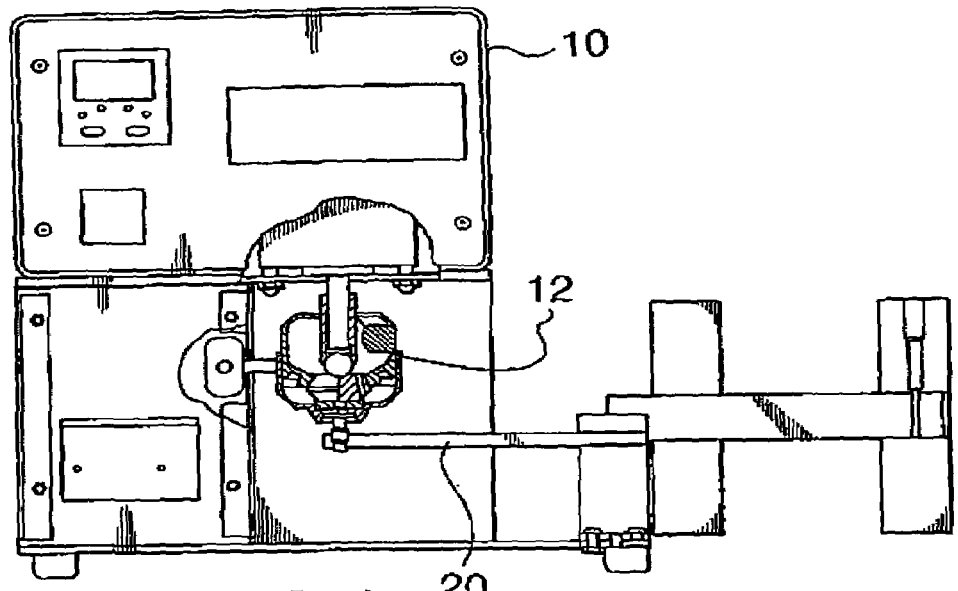
FIG. 1 illustrates a Ball on Three Disks lubricity tester.
Figure 2:
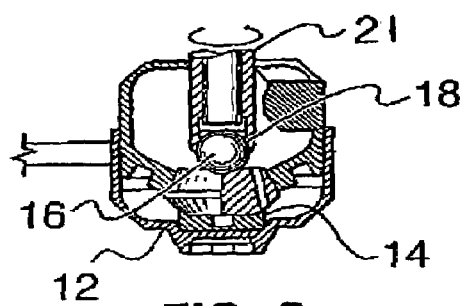
FIG. 2 illustrates a partial cross-sectional view of a specimen chamber of the tester of FIG. 1.
Figure 3:
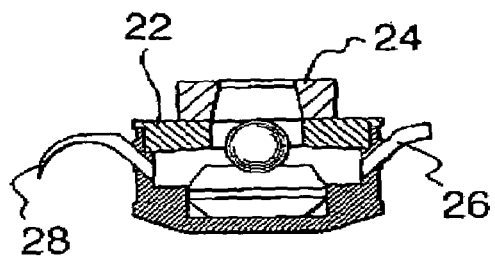
FIG. 3 illustrates a cup assembly for the specimen chamber of FIG. 2 in accordance with teachings of this invention.
Figure 4:
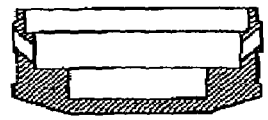
FIG. 4 illustrates a cup of the cup assembly of FIG. 3.
Figure 6:
FIG. 6 illustrates a bushing of the cup assembly of FIG. 3.
Figure 5:
FIG. 5 illustrates a cup of the cup assembly of FIG. 3.

Referring to FIG. 1, there is shown a Ball on Three Disks (BOTD) lubricity tester 10. The tester includes a one-piece fuel reservoir 12 (seen in more detail in FIG. 2) in which the fuel to be tested is dispensed with a syringe for testing. The fuel reservoir houses the metal disk holder 14, three steel test disks 16 (typically in a tetrahedral orientation), a ceramic ball 16, and the test fuel sample.

A lever arm 20 extends outwardly from the tester, and has a fulcrum, a weight suspended therefrom, and a Teflon pad at one end which is used to apply a force to the bottom of the 1 piece fuel reservoir. The weight is typically a 2.5 kg weight which is applied to the system during testing. The system also includes a timer; each test is typically run for 45 minutes.

The machine also includes a ball chuck 18 which secures the ceramic ball 16. The ball is typically about half an inch in diameter. The shaft 21 extends upwardly from the ball and out from an opening in the top of the machine.

A torque clamp projects outwardly from one side. A bolted load pin pivot block secures the fuel reservoir to the load pin assembly. There is also a large glass syringe, Teflon™ (polytetrafluoroethylene tubes and 5 micron Teflon™ filter.

The inventors have found unexpectedly that variations in the moisture content are the cause of inconsistent results obtained from this testing procedure. The prior art BOTD system allows direct contact between the fuel and ambient air, thereby skewing the true lubricity characteristics of the fuel depending on how much ambient moisture is picked up during the testing procedure. In one embodiment of the BOTD system according to the principles of the invention, contact is essentially eliminated between a test fuel and the ambient air around the BOTD test machine. It has been found that using means to control the moisture content (entering or leaving the fuel), can minimize the variations in results form one sample to the next.

Referring to FIGS. 3 to 6, there is shown a moisture blocking means for use in a specimen chamber in accordance with principles of the invention. In one embodiment, the moisture blocking means includes a fuel reservoir cover 22 with internal taper (which is preferably aluminum or stainless steel). On top is placed a fuel reservoir cover seal 24 (preferably Teflon™). A fuel inlet 26 and an outlet 28 are provided. Features of the BOTD that isolates the test fuel from ambient test conditions in this embodiment include the fact that:

the fuel reservoir cover has an inside taper which directs air out of the chamber during filling of the chamber with fuel, thereby eliminating the potential for air pockets;

the fuel reservoir extends beyond the height of the inside taper when assembled allowing the chamber to be filled completely with fuel;

there is a very close fit between the fuel reservoir and fuel reservoir cover thereby minimizing the quantity of fuel exposed to ambient conditions and ensuring that the exposed fuel in this gap cannot travel back inside the fuel reservoir;

there is a moderate sized gap (>0.020") between the test machine shaft and fuel reservoir cover which allows air that migrates up the fuel reservoir cover inside taper to escape;

the fuel reservoir inlet and outlet fittings ensure the proper height of fuel within the fuel reservoir during filling and testing;

the fuel reservoir outlet fitting prevents a siphoning effect when the fuel is redirected for deposit into a waste container. A siphoning effect can pull air into the fuel reservoir; and a very close fit is provided between the fuel reservoir cover and fuel reservoir cover seal, thereby minimizing the quantity of fuel exposed to ambient conditions and ensuring that the exposed fuel in this gap cannot travel back inside the fuel reservoir.

The fuel reservoir cover seal inside taper allows air to migrate out of the fuel reservoir through a moderate sized gap (>0.020") between the seal and shaft along the lower portion of the seal. A small gap is not used in this area since once the chamber is nearly full, fuel resides in this gap which prevents the last of the air from escaping due to the viscosity effects of the fuel.

Significant flushing of the fuel reservoir is provided. Once the fuel reservoir is filled with fuel, fuel flow continues to displace the fuel in the chamber which has made contact with the initial air in the chamber during the filling process. The excess fuel exits the fuel reservoir outlet fitting into a waste fuel container. Currently 105 ml of fuel is supplied to the fuel reservoir, 90 ml goes to a waste reservoir and 15 ml remains within the fuel reservoir.

In this way, the test chamber is blocked, preventing the fuel to be tested from coming into contact with air, and thus controlling the moisture content of the fuel. It has been determined that when the moisture/humidity is controlled, the results obtained are more accurate with lower levels of variation. Therefore, variations in results can safely be attributed to fuel quality rather than mere changes in humidity.

Upon completing an intensive cleaning procedure the BOTD components are assembled for testing. The disk holder is placed into a depression located at the inside bottom center of the fuel reservoir. The depression is concentric with the chamber and the disk holder thereby preventing lateral movement of the disk holder. The 3 test disks are then placed in the disk holder. The ceramic test ball is placed in the lower end of the hollow (internal taper) shaft of the test machine.

The fuel reservoir cover is then placed on the fuel reservoir and the fuel reservoir cover seal slid over top of the test machine shaft. The base of the fuel reservoir is then placed on top of the Teflon™ pad on one end of the lever arm. The lever arm is then placed in the fulcrum with the weight nearest the fulcrum. The lever arm and fuel reservoir assembly is ten rotated such that the test machine shaft and test ball assembly passes through the opening in the fuel reservoir cover, until the test ball contacts the test disks. The fuel reservoir cover seal is the lowered down the shaft onto the fuel reservoir cover.

Fuel is withdrawn from its fuel storage container using the large glass syringe such that air is not allowed to enter the fuel in the syringe. A 5 micron filter is attached to the syringe then a Teflon™ tube is used to attach the filter to an inlet on the fuel reservoir, A force (gravitational or otherwise) is applied to the syringe causing the fuel to transfer from the syringe to the filter, through the Teflon™ tube and to the fuel reservoir inlet fitting. As the fuel reservoir fills, the air in the fuel reservoir is displaced through an outlet fitting—in the fuel reservoir and through a small clearance gap between the fuel reservoir and cover, as well as the small clearance gap between the fuel reservoir cover seal and test machine shaft. Due to the taper in the cover all of the air in the fuel reservoir is displaced by the fuel, unlike the old BOTD in which a significant portion of the chamber contained ambient air from the test machine surroundings.

Once the fuel reservoir is filled with fuel, fuel flow continues to displace the fuel in the chamber which has made contact with the initial air in the chamber during the filling process. The excess fuel exits the fuel reservoir outlet fitting into a waste fuel container. Currently 105 ml of fuel is supplied to the fuel reservoir, 90 ml goes to a waste reservoir and 15 ml remains within the fuel reservoir.

Upon completion of the fuel transfer, the test machine is set for 45 small clearances and the start button pressed causing the test machine ball and shaft to rotate with the ball contacting the disks during rotation. The weight on the lever arm is then gradually pulled towards the outer end of the lever arm, thereby increasing the force applied to the fuel reservoir at the opposite end of the lever arm and correspondingly the contact force between the disks and ball. During the test, the small clearance gaps between the fuel reservoir and cover, as well as the fuel reservoir cover seal and test machine shaft prevent air from the surroundings from interacting with the test fuel. As such, the fuel humidity characteristics during the test are the same as within the fuel storage container.

Upon completion of the test, the assemblies are disassembled and the disks removed for evaluation. Due to the relative motion and contact force between the ball and disks during the test a wear scar is generated on the metal disks. The fuel in the fuel reservoir provides some measure of lubrication between the ball and disks. As such the size of the wear scar on the disks is related to the lubricity characteristics of the fuel. The disks are placed in a holder, and a traveling microscope with dial indicator is used to determine the diameter of the wear scar on the disks. A large wear scar indicates a fuel with poor lubricity and a small wear scar indicates a fuel with good lubricity.

The prior art BOTD system attempted to provide consistent wear scar data by controlling the laboratory conditions to a fixed value [45% relative humidity (RH.)]. Recent testing indicated that significant changes in the laboratory RH. resulted in significant changes in the wear scar diameters. Lower RH. values generated smaller wear scars, thereby indicating improved fuel lubricity as water vapor was removed from the fuel. R.H. testing of fuel storage containers indicated that fuel in a storage container could be exposed to significantly different RH. values than the fixed laboratory conditions. As such, a fuel exposed to a low RH in the original storage container would have better lubricity than indicated by the old BOTD test which would expose the fuel to higher RH. conditions during the test.

The BOTD system in accordance with the principles of the invention is designed to eliminate the effect of ambient humidity conditions on the test fuel, whether the test is performed in the laboratory or in the field. The BOTD system eliminates the need for ambient humidity control and provides a lubricity value which is consistent with the fuel storage container conditions instead of the ambient conditions.

As indicated in the Table shown in FIG. 7, the BOTD system isolates the fuel from the ambient conditions and provides a lubricity value which is consistent with the fuel storage container conditions. In addition, the new BOTD system has shown greater response to the addition of some lubricity additives (LAs) which are typically used to improve the lubricity of diesel fuel. The * in FIG. 7 indicates that the Ambient RH. during the test was 23% instead of 45%. Practically, the fuel may already have moisture therein. It can also be useful to measure the lubricity of dry fuel. It has also been determined that fuel can be dried easily in a few minutes by placing it in the presence of a desiccant. Therefore, a desiccant may be provided to ensure that no additional moisture gets in if any air does contact the fuel. Then the disclosed system can be used to measure the lubricity of the dry fuel.

Figure 8:
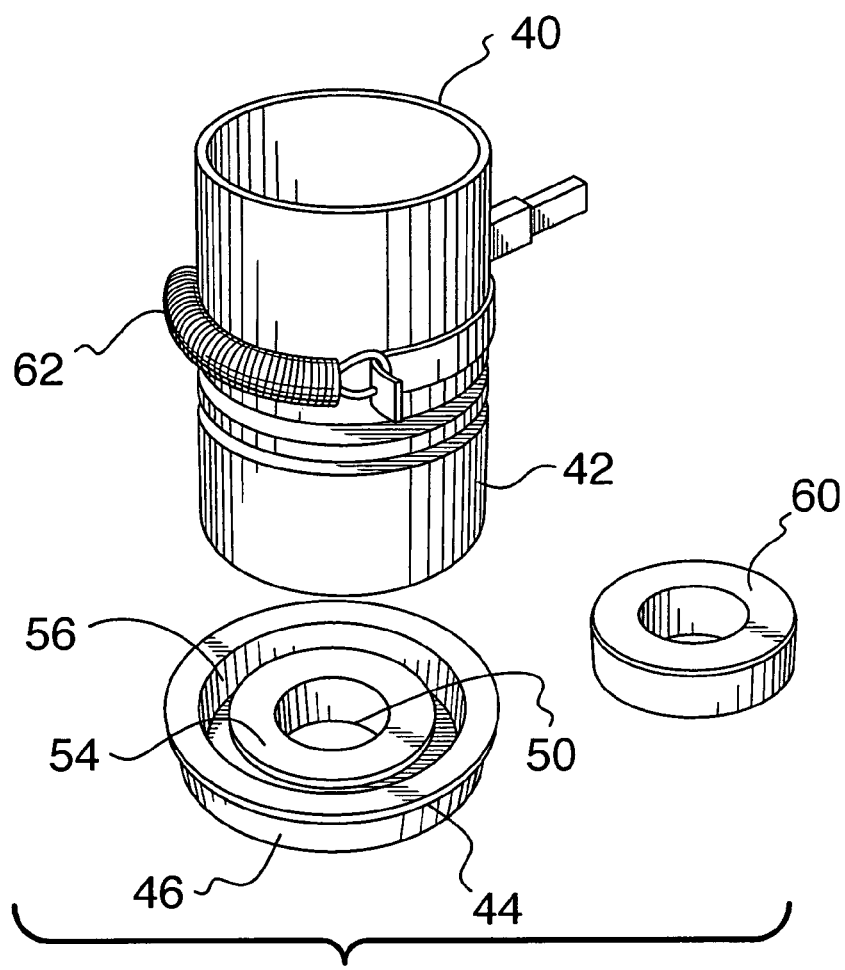
FIG. 8 is an exploded perspective view of a reservoir assembly in accordance with a second embodiment of the invention.
Figure 9:
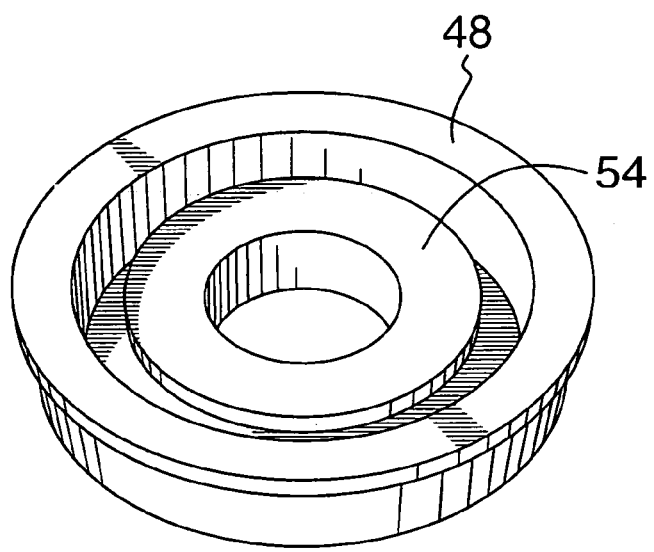
FIG. 9 is a close-up perspective view of the lid for the reservoir assembly.
Figure 10:
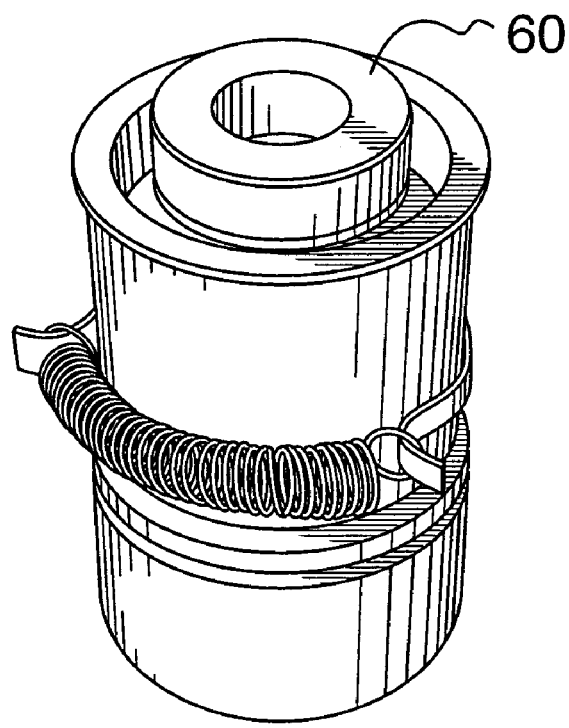
FIG. 10 is a perspective view of the assembled reservoir.

In the second embodiment shown in FIG. 8, the fuel tester includes a cylindrical reservoir 40 with a tapered bottom sitting on a supporting cylinder 42. The ball and chucks are located in the bottom of the reservoir in the same manner as in FIG. 2.

Figure 11:
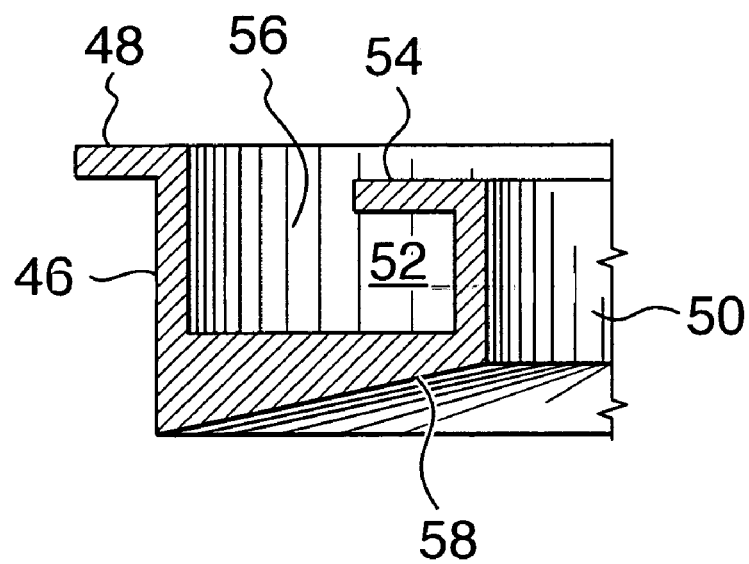
FIG. 11 is a partial cross section of the lid for the second embodiment of the invention.

The reservoir 40 includes a removable lid 44, which has an outer upstanding cylindrical wall 46 terminating in flat rim forming a flange 48 as shown more clearly in FIG. 11.

The lid has a central aperture 50 surrounded by an upstanding cylindrical collar 52 terminating at its upper end in flat rim 54 defining an overhanging flange. The rim 54 lies slightly below the rim 48.

The central collar 52 and upstanding wall 46 define between them a circular channel 56.

The bottom surface 58 of the lid 44 is inclined upwardly and inwardly at an angle that in this embodiment is 5°, although other angles up to about 15° can be used. The purpose of the incline is to cause any bubbles in the fuel within the reservoir 40 to migrate up toward the central hole 50 and thus escape from the reservoir. However, if the inclination is too great it becomes impractical to make all the components fit together properly.

In order to test fuel, the lid 44 is first placed on the reservoir 40. Fuel is carefully drawn into a syringe without introducing moisture or air and injected through the hole 50 into the reservoir 40 until it passes up the central hole 50 and overflows into the channel 56.

Any air or moisture bubbles in the fuel strike move upwardly until they strike the bottom surface of the lid, and due to its inclination, migrate upwardly and inwardly toward the central hole 50.

Next, a Teflon™ ring 60 is placed on the spindle 62 (FIG. 1), which is inserted part way through the hole 50 into the reservoir 40. The spindle does not make contact with the ball at this point. With the spindle extending part way into the reservoir, typically terminating about ½" above the ball, the reservoir is placed on the ball and fulcrum mechanism, which is raised into place. As the ball and fulcrum mechanism is raised, the spindle penetrates further into the reservoir so as to make contact with the ball 16. The ring 60 is then slid down the spindle until it contacts the flange 48, where it makes a fluid seal with the overflowing fuel.

The ring 60, which makes a fluid seal with the spindle, is then slightly lifted by hand to exert a pumping action on the fuel within the reservoir 40, which has the effect of further drawing out any remaining air bubbles that might be trapped within.

After returning the ring 60 to its position on the flange 48 the spindle is rotated and the measurement carried out in an otherwise conventional manner.

Although the ring 60 makes a fluid tight seal with the spindle, it does not rotate with it.

The reservoir also includes a spring 62 that clamps the reservoir and prevents rotation as the spindle turns.

Experiments have shown that the above method results in a particularly reliable and repeatable set of measurements. The incline on the bottom of the lid has proved particularly effective in ensuring consistency because of the way in which it helps to eliminate any residual air bubbles.

Numerous modifications may be made without departing from the spirit and scope of the invention as defined in the appended claims.

We claim:

1. A method of testing the testing lubricity of a fuel, comprising the steps of:
   extracting a fuel sample from a source of fuel to be tested;
   transferring said fuel sample to a testing chamber without exposing said fuel sample to ambient air; and
   performing a lubricity test on said sample in said testing chamber without exposing said fuel sample to ambient air so that the moisture content of the fuel in said sample is substantially the same as the moisture content of the fuel in said source.

2. The method of claim 1, wherein said fuel is tested using a BOTD method.

3. The method of claim 1, wherein said fuel is transferred to said testing chamber with a syringe.

4. An apparatus for testing lubricity of a fuel, comprising: a testing chamber for holding a sample of the fuel to be tested; a lid for closing said chamber, said lid including an aperture for the introduction of fuel into said chamber and subsequently accommodating a drive spindle, and said lid having a bottom surface that is inclined upwardly and inwardly toward said central aperture; and an element for sealing the testing chamber to prevent moisture transfer during admission and testing of the fuel.

5. The apparatus of claim 4, wherein said bottom surface is inclined at an angle of about 5 to 15°.

6. The apparatus of claim 5, wherein said element is ring.

7. The apparatus of claim 6, wherein said element is a polytetrafuoroethylene ring.

8. The apparatus of claim 4, wherein said lid comprises an outer upstanding cylindrical wall and a central collar surrounding said aperture, said cylindrical wall and collar defining between them a channel.

9. The apparatus of claim 8, wherein said central collar extends upwardly from the bottom of said lid by an amount less than said cylindrical collar.

10. A method of testing the lubricity of a fuel, comprising:
    extracting a fuel sample from a source of fuel to be tested;
    transferring said fuel sample to a testing chamber without exposing said fuel sample to ambient air, said fuel sample being transferred through an aperture in a lid with an aperture, said lid having an inclined bottom surface extending upwardly and inwardly toward said aperture;
    allowing any bubbles in said fuel sample to migrate upwardly and out through said aperture;
    inserting a spindle into said aperture, said spindle having a sealing ring therearound for sealing said aperture; and
    performing a lubricity test on said sample in said testing chamber without exposing said fuel sample to ambient air so that the moisture content of the fuel in said sample is substantially the same as the moisture content of the fuel in said source.

11. The method of claim 10, wherein said sealing ring is made of polytetrafuoroethylene.

12. The method of claim 10, wherein said sealing ring rests on a collar surrounding said aperture, and prior to performing said lubricity test said sealing ring is lifted off said collar to exert a pumping action on any air bubbles remaining within said fuel sample to extract them through said aperture.

13. The method of claim 12, wherein said fuel is inserted into said testing chamber with a syringe.

* * * * *